(12) United States Patent
Baege et al.

(10) Patent No.: US 8,377,376 B2
(45) Date of Patent: Feb. 19, 2013

(54) IMPLANT AND A METHOD OF MANUFACTURING AN IMPLANT PACKED IN A STERILE MANNER

(75) Inventors: Roland Baege, Wiesendangen (CH); Hermann Breimesser, Elgg (CH); Roland Willi, Neftenbach (CH)

(73) Assignee: Zimmer GmbH, Winterthur (CH)

( * ) Notice: Subject to any disclaimer, the term of this patent is extended or adjusted under 35 U.S.C. 154(b) by 573 days.

(21) Appl. No.: 12/274,602

(22) Filed: Nov. 20, 2008

(65) Prior Publication Data
US 2009/0081076 A1 Mar. 26, 2009

Related U.S. Application Data

(62) Division of application No. 10/410,079, filed on Apr. 9, 2003, now Pat. No. 7,473,279.

(30) Foreign Application Priority Data

May 31, 2002 (EP) .................................... 02012124

(51) Int. Cl.
*A61F 2/30* (2006.01)
*A61L 2/20* (2006.01)
(52) U.S. Cl. ..................................... 422/34; 623/23.43
(58) Field of Classification Search ................ 422/1, 28, 422/32, 34; 623/22.11, 22.15, 22.17, 22.18, 623/22.19, 22.2, 22.21, 22.22, 22.23, 22.24, 623/22.25, 22.26, 22.27, 22.28, 22.29
See application file for complete search history.

(56) References Cited

U.S. PATENT DOCUMENTS

| 1,489,642 | A | 4/1924 | Kendall |
| 3,818,514 | A | 6/1974 | Clark |
| 3,863,273 | A | 2/1975 | Averill |
| 4,065,816 | A | 1/1978 | Sawyer |
| 4,705,518 | A * | 11/1987 | Baker et al. ................ 623/14.13 |
| 5,019,105 | A | 5/1991 | Wiley |
| 5,062,853 | A | 11/1991 | Forte |
| 5,246,462 | A | 9/1993 | Bekki et al. |
| 6,007,580 | A | 12/1999 | Lehto et al. |
| 6,165,220 | A | 12/2000 | McKellop et al. |
| 6,358,282 | B1 | 3/2002 | Wymann |
| 6,379,389 | B1 | 4/2002 | Koch |
| 6,379,615 | B1 * | 4/2002 | Ogle ............................... 422/28 |
| 6,527,809 | B1 | 3/2003 | Doursounian et al. |
| 7,025,787 | B2 | 4/2006 | Bryan et al. |
| 7,981,158 | B2 * | 7/2011 | Fitz et al. ................... 623/17.16 |
| 8,105,382 | B2 * | 1/2012 | Olmos et al. ............... 623/17.15 |

FOREIGN PATENT DOCUMENTS

| EP | 0729981 | 9/1996 |
| EP | 0923945 A2 | 6/1999 |

(Continued)

OTHER PUBLICATIONS

Reprint from beta-gamma 1/89 of article entitled Investigation on Sterilization and Modification of High Molecular Weight Polyethylenes by Ionizing Irradiation, by Robert M. Streicher, Sulzer AG, CH-8401 Winterthur, Switzerland (10 pp), Jan. 1989.

*Primary Examiner* — Anu Ramana
(74) *Attorney, Agent, or Firm* — Schwegman, Lundberg & Woessner, P.A.

(57) ABSTRACT

An implant is set forth having at least one first element and a second element, wherein the first element is provided in a pre-determined relative location to the second element, in particular at least partly in a recess of the second element. The first element has a pre-positioning location having play with respect to the second element and allowing a fully area gas sterilization of both elements and can be displaced from this pre-positioning location into an end positioning location corresponding to a fixed connection of both elements.

24 Claims, 11 Drawing Sheets

FOREIGN PATENT DOCUMENTS

| | | |
|---|---|---|
| GB | 1489642 | 10/1977 |
| WO | WO-9427651 | 12/1994 |
| WO | WO-9729793 | 8/1997 |
| WO | WO-9814223 | 4/1998 |
| WO | WO0009045 A1 | 2/2000 |
| WO | WO0180778 A1 | 11/2001 |

\* cited by examiner

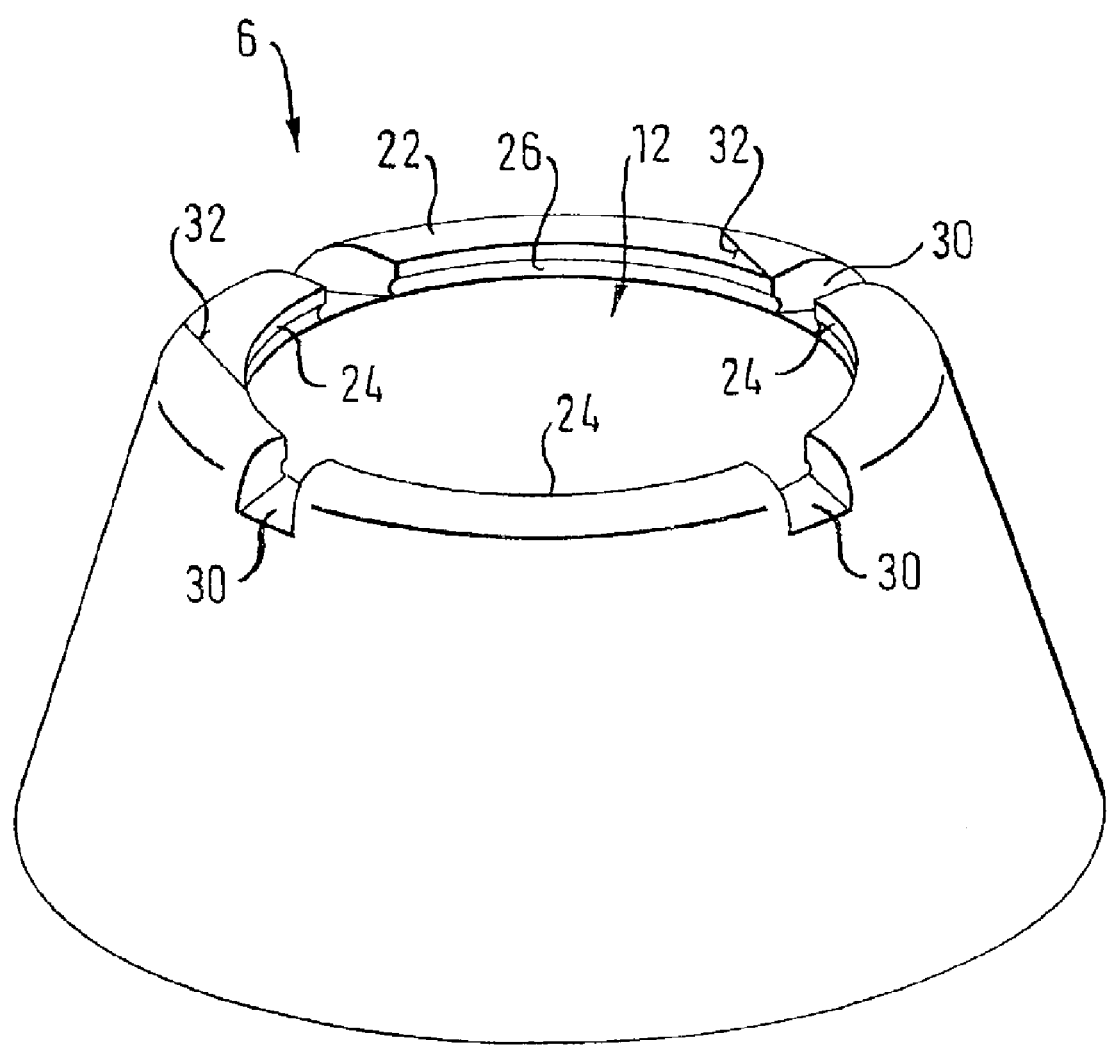

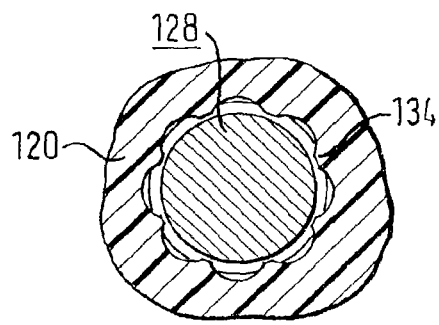
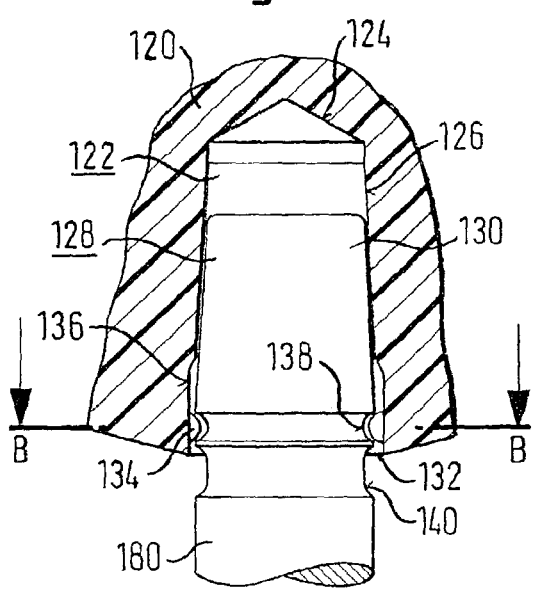
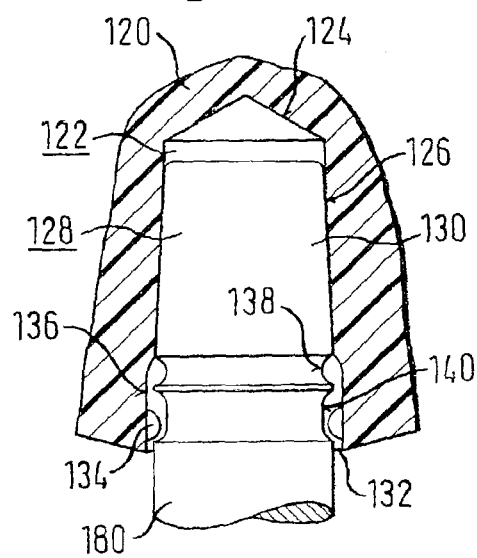

Fig. 10b
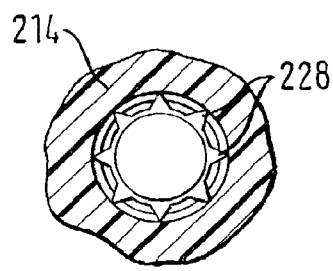
Fig. 10d
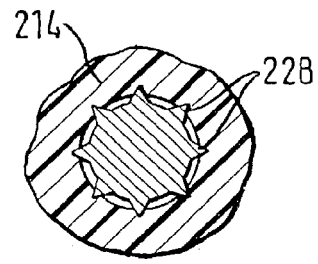
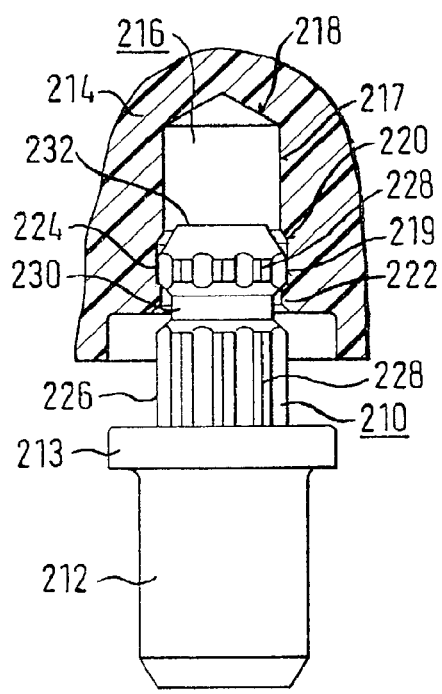
Fig. 10a
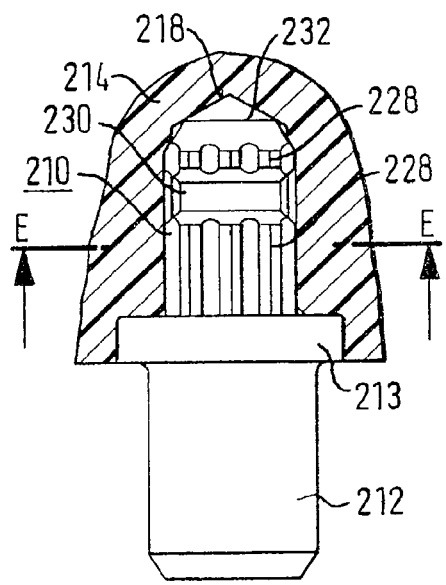
Fig. 10c

IMPLANT AND A METHOD OF MANUFACTURING AN IMPLANT PACKED IN A STERILE MANNER

CROSS REFERENCE TO RELATED APPLICATIONS

This application is a division of U.S. patent application Ser. No. 10/410,079, entitled "Implant and a Method of Manufacturing an Implant Packed in a Sterile Manner," filed on Apr. 9, 2003 by the same inventors hereof, the disclosure of which is expressly incorporated herein by reference.

BACKGROUND

1. Field of the Invention

The invention relates to an implant and to a method of manufacturing an implant packed in a sterile manner.

2. Description of the Related Art

Ultra-high molecular weight polyethylene (UHMWPE) is a material widespread in orthopaedic endoprosthetics which has proven itself as a sliding partner with respect to metallic and ceramic materials. A problem with these material pairings is the wear unavoidable in use and the particle-induced osteolysis triggered thereby which in the worst case can result in a loosening of the implant.

A suitable measure for the optimization of the UHMWPE with the aim of reducing the arising wear is high cross-linking. This is achieved by electron radiation or gamma radiation and a heat treatment of the material, whereby the ultra-high molecular weight polyethylene is made wear resistant and given long term stability. The high cross-linking takes place by a cross-linking of the UHMWPE molecule chains and by a de-saturation of the free radicals.

The sterilization method of gamma radiation usual in orthopaedic endoprosthetics cannot be used for highly cross-linked UHMWPE, because unwanted free radicals would again thereby arise. These free radicals promote an oxidation effect and an embrittlement of the associated material. Highly cross-linked UHMWPE is therefore not sterilized with ionizing radiation, but with gas, for example with ethylene oxide or gas plasma.

With implant components which consist exclusively of highly cross-linked polyethylene, satisfactory results are achieved by means of high cross-linking and heat treatment of the UHMWPE blank, subsequent mechanical processing, packaging and gas sterilization.

However, implants can consist of a plurality of elements put together during the manufacturing process. With such composite implants, the problem of effective sterilization arises. A sterilization with gamma rays would cover the whole implant and thus oxidize elements made of UHMWPE. A gas sterilization, in contrast, only acts on all those surfaces of the implant which are accessible to the gas during the sterilization. To also make surfaces covered by additional elements accessible to the sterilizing gas, it is known in this connection to carry out the connection of implant elements with play. However, such play is problematic on the basis of clinical experience, since micro-movements of implant elements made possible in this manner are under suspicion of producing unwanted wear and of countering a permanent ingrowth of the bone.

SUMMARY

It is an object of the present invention to set forth a multi-part implant which allows an effective sterilization and a maintenance of the sterile state up to the practical use of the implant.

This object is in particular satisfied in that, with an implant with at least a first element and a second element, with the first element being provided in a pre-determined relative position to the second element, in particular at least partly in a recess of the second element, the first element has a pre-positioning location with respect to the second element, which has play and ensures a fully area gas sterilization of both elements, and can be displaced from this pre-positioning location into an end positioning location corresponding to a fixed composite of both elements.

If the multi-part implant is packaged in a pre-determined pre-positioning location for the first element and if a gas sterilization is subsequently carried out while the first element is disposed in the defined pre-positioning position, an extremely effective, full area sterilization of the multi-part implant can be achieved. The sterilized implant is transported and stored in the packaging in this pre-installed position until it is brought, as required, to the operational field where it is available in the pre-installed state after the tearing open of the packaging.

It is ensured with the implant in accordance with the invention that the time difference between the sterilization and the operation cannot have any disadvantageous effects. The play present at the time of the gas sterilization and during the storage or the transport between the individual elements mechanically connected to one another can be simply eliminated by displacement of the first element from the pre-positioning location into the end positioning location and the first element can be reliably fixed in place with respect to the second element for implanting. A complicated unpacking and putting together of individual elements of the implant, wherein the implant could be contaminated, is thus not necessary.

Furthermore, in an embodiment of the implant in accordance with the invention in which the first element is provided at least partly in a recess of the second element, the first element can be held loosely in the pre-positioning location in the recess, with the contact points between the first element and the second element in the recess being small in area, and can be connected to the second element in a force locked and shape matched manner in an end positioning location in the recess. The first element is in this connection displaceable from the pre-positioning location into the end positioning location in the recess.

Since the first element is held loosely in the recess in the pre-positioning location and the contact points between the first element and the second element in the recess are small in area, practically all surfaces of the first element and of the second element can be reached by sterilizing gas. At the same time, the play in the pre-positioning location is sufficient to make the surfaces of the implant accessible to the sterilizing gas during the sterilization process, but small enough to avoid any unwanted wear on vibrations of the implant. The force locked and shape matched connection of the elements in the end positioning location moreover allows a reliable use of the inserted implant according to its function.

The material of at least one of the first and second elements can include highly cross-linked ultra-high molecular weight polyethylene and/or another plastic. These materials can be used because the implant in accordance with the invention allows an extremely effective gas sterilization of such pre-installed plastic parts.

The material of one of the first and second elements can furthermore include a metal, in particular titanium. Accordingly, implants can be formed in accordance with the invention, and thus also be reliably sterilized with gas, which have elements of different material combinations.

In an embodiment, the first element can be held loosely in a substantially centered manner in the pre-positioning location. This centering allows a play which is equally low on all sides between the elements so that all surfaces of the implant can be reached by the sterilization medium during the gas sterilization.

The first element can be held in the pre-positioning location with a play of at least 0.1 mm, for example 0.2 to 0.4 mm. This play allows the accessibility of practically all surfaces of the implant and thus a reliable gas sterilization, a sterile storage and a sterile transport in the packaged state.

The recess can have a substantially circular cross-section, the first element can have a substantially circular and/or substantially star-like cross-section, and the first element can be held radially and axially loosely in the recess in the pre-positioning location. It is achieved in this way that, with a recess and a first element with circular cross-sections, play is present both radially and axially between the first element and the second element which allows an effective gas sterilization of all surfaces of the implant.

The contact points between the first element and the second element in the recess can in particular be substantially punctiform. The size of the contact areas between the first element and the second element can thereby be minimized such that, taking into account the low relative movability between the elements, the sterilization medium can flow about all surfaces of the implant during the gas sterilization.

Furthermore, the number of contact points in the recess between the first element and the second element in the pre-positioning location is kept low. This also results in the fact that the contact area between the first element and the second element is kept as small as possible so that the sterilization medium can flow ideally about the implant.

In an embodiment, the first element is held loosely in the pre-positioning location by means of a snap connection and, in the end positioning location, is connected in a force locked and shape matched manner to the second element in a clamping fit and/or by means of a snap connection. The first element can thereby be moved from the pre-positioning location into the end positioning location, in which the first element is fixed in the second element, by a simple displacement such as a rotation and/or shift.

Furthermore, the first element can have at least one projection which engages into the second element in the end positioning location. This ensures a secure force locked and shape matched connection of the first element to the second element of the implant.

The first element can moreover be a ball or a pin, in particular a metal ball or a metal pin. For example, X-ray contrast balls or pins can thus be effectively sterilized with gas in an implant and be reliably fixed in the implant before the operation.

The first element can include a ball and a plug with a receiver for the ball. The ball can be held loosely in the plug, or between the plug and the recess, in the pre-positioning position and the plug can be held in a force locked and shape matched manner in the recess and the ball in the plug in the end positioning location. With this embodiment, tiny balls, for example with a diameter of 2 mm, can be reliably sterilized together with the implant and can be reliably fastened in the implant intraoperationally. At the same time, the handling of the balls and the keeping of them sterile during the handling is simplified.

In a further embodiment, the second element can be an inner shell of a joint prosthesis and the first element can be a cover plate of the inner shell. The recess can be provided in the outer wall of the inner shell having a circular cross-section, a side wall and a base becoming deeper towards the centre of the recess, with the side wall having at least one holding projection directed towards the centre of the recess. The cover plate can be loosely held by the side wall and the projection and can have at least one cam at its outer periphery which engages clampingly into the side wall of the recess in the end positioning location when the cover plate is displaced from the pre-positioning location into the end positioning location by a rotational movement.

This design, for example makes possible a highly effective sterilization with gas with a truncated conically shaped hip joint prosthesis shell with a cover plate since the cover plate is mounted with sufficient play in the pre-positioning location. The contact between the first element and the second element is kept to a small area by the base becoming deeper toward the centre of the recess, by the planar form of the cover plate and by the projection. The gas reaches the base through grooves which interrupt the side wall and reach up to the base. A flowing around the cover plate in the recess on all sides is thus achieved during the gas sterilization. The at least one cam of the cover plate moreover ensures an extremely fixed connection between the first element and the second element in the end positioning location.

At least one receiver for the cam in the side wall of the recess can be provided with play in the pre-positioning location. It is thereby made possible that the sterilization medium also flows sufficiently around the cam region during the gas sterilization in the pre-positioning location.

The side wall of the recess can moreover have a guide, in particular an insert guide, for the insertion of the first element into the pre-positioning location. This facilitates the installation of the first element in the second element before the carrying out of the gas sterilization.

The object is moreover in particular satisfied in that, for the manufacture of an implant packaged in a sterilized manner having at least one first element and one second element, the elements forming the implant can be sterilized with gas in a mutually coupled pre-positioning location having play relative to one another and can be inserted up to and into the actual operational field in this pre-positioning location.

The gas sterilization can be carried out with ethylene oxide.

The individual elements packaged in a sterile manner in a pre-positioning location can be connected to one another in a force locked and shape matched manner for the final installation of the implant after opening the package by rotational and/or displacement movements.

Finally, the invention includes a packaging with a gas permeable membrane which is impermeable to micro-organisms, containing an implant made of a plurality of individual elements with which the individual elements can be sterilized with sterilizing gas in mechanically coupled manner and with mutual play in a pre-positioning location from which they can be moved into an end positioning location mutually connected in a force locked and shape matched manner after the opening of the packaging by rotational and/or displacement movements.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIGS. 1a, 1b are cross-sectional views of a first embodiment of an implant in accordance with the invention and an associated perspective plan view;

FIGS. 7a-7c are cross-sectional views of a seventh embodiment;

FIGS. 10a-10d are cross-sectional views of a tenth embodiment.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

First Embodiment

Figure 1A:
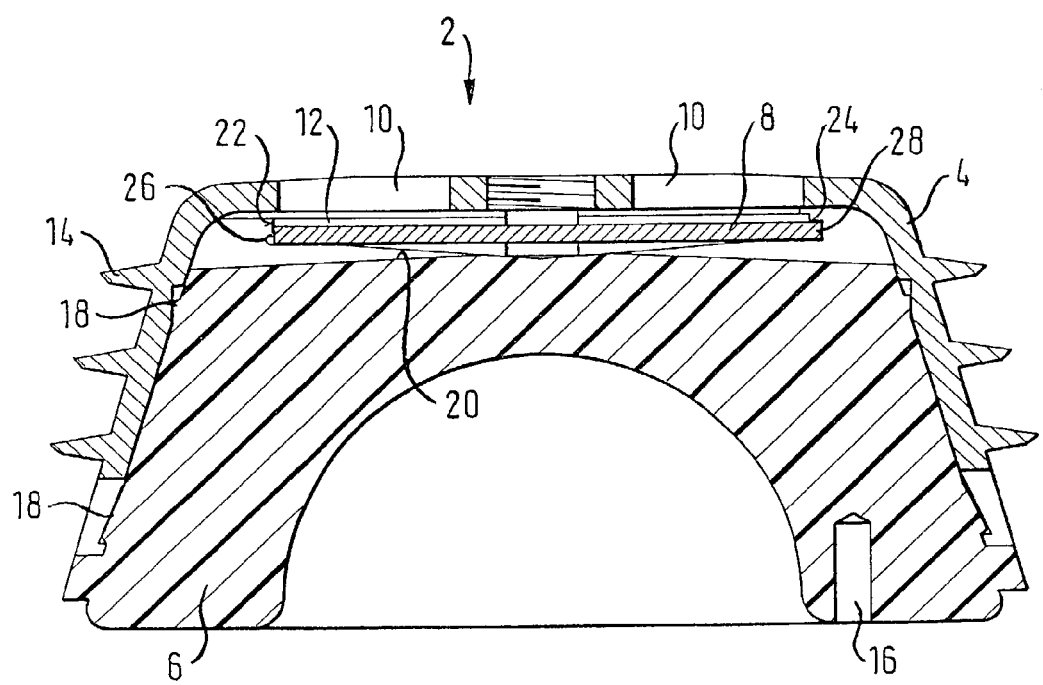

A first embodiment of the implant in accordance with the invention shown in FIGS. 1a and 1b in the end positioning location consists of a truncated conically shaped hip joint prosthesis shell 2 having an outer shell 4 of titanium, an inner shell 6 of highly cross-linked ultra-high molecular weight polyethylene (UHMWPE) and a cover metal sheet 8 of titanium. The hip joint prosthesis shell 2 is formed as an acetabulum which is implanted without the use of bone cement. Openings 10 in the outer shell allow the seating of the shell in the bone to be controlled and any hollow spaces to be filled with bone shavings. To prevent a direct contact of the bone with the polyethylene of the inner shell 6 through the openings 10 of the outer shell, the cover metal sheet 8 is provided made of the bio-compatible material titanium. This is located in a recess 12 of the inner shell and is centered in this recess 12.

As can be seen from FIG. 1a, the outer shell 4 has a self-tapping thread 14 for the anchoring of the acetabulum in the bone. Bores 16 are provided at the lower side of the inner shell 6 and serve for the insertion of a tool. The inner shell 6 is fastened in the outer shell 4 by means of a snap connection 18 consisting of depressions on the inner side of the outer shell 4 and projections on the outer side of the inner shell 6.

FIG. 1a shows that the recess 12 has an inclined base 20 which is lowered toward the centre of the inner shell 6. The recess 12 is bounded by a side wall 22 at whose upper end, roughly in one peripheral half of the recess, an inwardly directed projection 24 is provided. This projection 24 engages over the cover metal sheet 8 when this is inserted into the recess 12 from the side lying opposite the projection 24.

FIG. 1b shows a perspective side view of the inner shell in which the cover metal sheet is not inserted. As can be seen from this illustration, four radially extending grooves 30 arranged offset to one another by 90 degrees are provided in the side wall 22. Additionally, two insert guides 32 for the cover metal sheet 8 are provided adjacent to the ends of the projection 24. The insert guides 32 are formed such that they guide the cover metal sheet 8 underneath the projection 24 on insertion into the recess 12.

Furthermore a peripheral groove 26 is provided in the recess 12 at the transition between the side wall 22 and the base 20.

The cover metal sheet 8 of planar form has an engagement cam 28 at its periphery. This one cam 28 can be recognized in FIG. 1a.

When the cover metal sheet 8 is inserted into the recess 12, the cover metal sheet is placed between the insert guides 32 onto the side wall 22 and pushed into the recess 12, with the cam 28 coming to rest in a groove 30. The cover metal sheet 8 is in this connection pushed under the projection 24 in the recess 12 and then adopts the pre-positioning location in which it is held loosely by the projection 24. The dimensions of the recess 12, the presence of the groove 26 and the inclined base 20 have the effect that the cover metal sheet 8 is held in the recess with a play of, for example, approximately 0.2 mm, on the one hand, and is supported exclusively in a small area manner, on the other hand. The cam 28 of the cover plate is in this connection loosely positioned in one of the grooves 30 of the side wall 22, i.e. the pre-positioning location is present.

For the fixed, i.e. force locked and shape matched connection of the cover metal sheet 8 to the inner shell 6, the cover metal sheet 8 is rotated using a tool such that the cam 28 digs into the side wall 22 and is immovably connected to this in the end positioning location of the cover metal sheet 8. This state is shown in FIG. 1a.

Markings which are not shown in FIGS. 1a, 1b, which are attached to the outside of the cover metal sheet 8 and which are arranged in a rotationally offset manner with respect to the grooves 30 in the pre-positioning location serve to ensure the reliable achievement of the end positioning location. To bring the cover metal sheet 8 into the end positioning location, the tool is inserted into the cover metal sheet 8 and the metal sheet is rotated until the markings on the cover metal sheet 8 and the grooves 30 are directly opposite one another.

The pre-positioning position of the cover metal sheet 8 is set at the implant manufacturer's before the sterilization of the inner shell with ethylene oxide. The gas sterilization is subsequently carried out. Since the contact areas between the cover metal sheet 8 and the inner shelf 6 in the recess 12 are kept to a minimum in the pre-positioning location due to the low play and the inclined base 20 of the recess, the ethylene oxide can practically flow around all surfaces of the cover metal sheet 8 and of the inner shell 6 taking into account the relative movability of the individual parts in the sterilization. An extremely effective and reliable gas sterilization is thus made possible.

For the known gas sterilization, the parts are already cleanly packaged in a plurality of packages lying inside one another which are closed by gas-permeable membranes. While these membranes allow gas molecules to pass, they do not allow any micro-organisms to pass. The parts packaged in this manner are flushed in a closed container with different bases at different pressures, with an actual toxic sterilizing gas, e.g. ethylene oxide, being applied to the parts at a high pressure in order to achieve sterility by killing off micro-organisms. This toxic gas must subsequently be removed through the membranes with following flushing procedures and at underpressure. At the end of the sterilization procedure, the sterile parts lie in a sterile packaging surrounded by air.

During the sterilization of the inner shell 6 packaged in the pre-positioning location, the play between the cover metal sheet 8 and the inner shell 6 allows the implant to be exposed over its full area to the sterilization gas. It is additionally avoided by the play kept small that the implant is impaired by movements during transport.

The packaging is opened shortly before the implanting or the insertion of the inner shell 6 into the already implanted outer shell 4 of the hip joint prosthesis 2 and the cover metal sheet 8 is rotated with the help of a sterile tool into the pre-determined end positioning location in which the cover metal sheet 8 is—as described—fixedly connected to the inner shell 6.

A complicated insertion of the cover metal sheet 8 into the inner shell 6 in the event of a separate packaging of the cover metal sheet 8, with the risk of the contamination of the implant, is thus avoided.

After the setting of the end positioning location of the cover metal sheet 8 in the inner shell 6, this is inserted into the outer shell using the aid of a tool, with the snap connection 18 becoming effective.

It is ensured in this manner that the parts brought together in a pre-positioning location are no longer separated from one another despite sterilization, transport and unpacking in the operation area. An association of parts is no longer necessary.

Second Embodiment

The second embodiment of the implant in accordance with the invention shown in FIGS. 2*a* to 2*d* includes an X-ray contrast ball 40 made of metal and an element 44 made of highly cross-linked ultra-high molecular weight polyethylene with a bore 42.

The bore 42 has a region 47 at its closed end with a diameter which has a small undersize with respect to the diameter of the ball 40. At its open end, the bore 42 has a region 49 with a diameter which is larger than the diameter of the ball 40.

Projections 46 and 48 are provided in the region 49 which are respectively spread over the periphery of the bore in an annular manner.

Figure 2A:
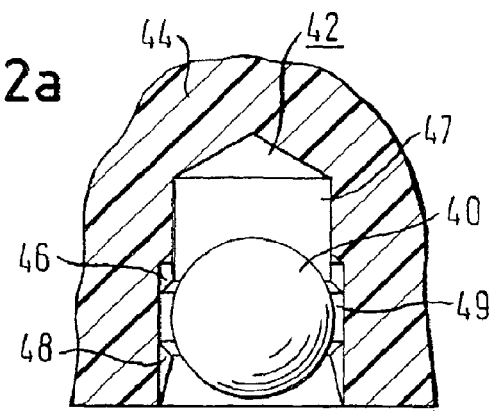
FIGS. 2a-2d are cross-sectional views of a second embodiment.

The pre-positioning location shown in FIG. 2*a* is set at the manufacturer's before the gas sterilization. In this connection, the X-ray contrast ball 40 is radially and axially loosely mounted between the projections 46 and 48. Moreover, only small-area contact points are present between the X-ray contrast ball 40 and the projections 46, 48. In addition, there is play on all side between the ball 40 and the element 44 of, for example, approximately 0.2 mm.

In the pre-positioning location, a sterilization is carried out with ethylene oxide gas in which practically all surfaces in the bore 42, including the X-ray contrast ball 40, are effectively sterilized.

Figure 2C:
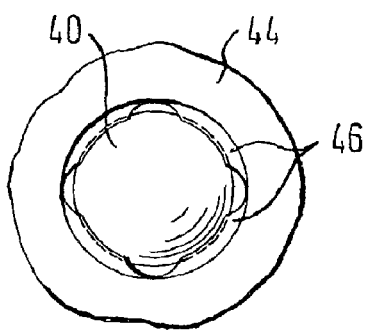
Figure 2B:
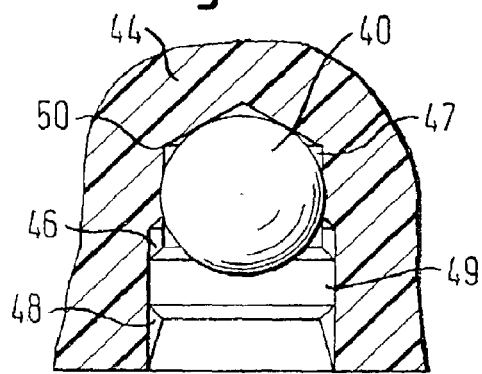

Shortly before the insertion of the implant, it is removed from the packaging with the loosely held X-ray contrast ball 40 and the ball is pressed to the end 50 of the bore into the end positioning location shown in FIGS. 2*b* and 2*c*. In this connection, the ball 40 is fixed in place at the closed end 50 of the bore in a clamped fit.

Figure 2D:
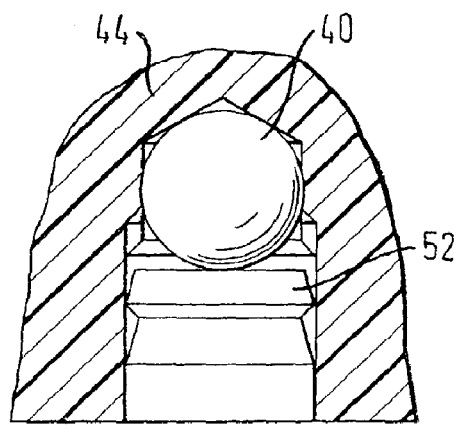

To press in the X-ray contrast ball 40, a separately supplied, sterile plug 52 can be used which is clamped in the end positioning location via projections 48 and is sealingly fixed in place in the bore 42. As shown in FIG. 2*d*, the plug 52 has such a length that a flush termination of the plug 52 with the open end of the bore 42 indicates that the ball 40 is fixed in place in its planned end position.

Third Embodiment

Figure 3A:
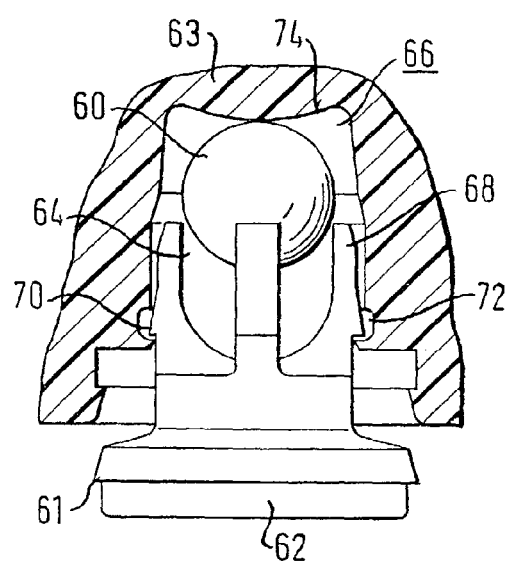
FIGS. 3a-3c are cross-sectional views of a third embodiment.
Figure 3B:
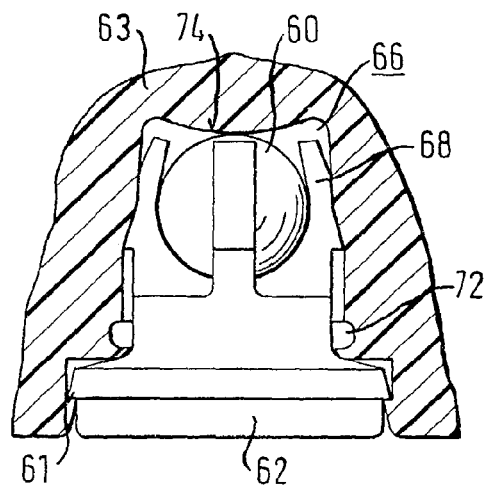
Figure 3C:
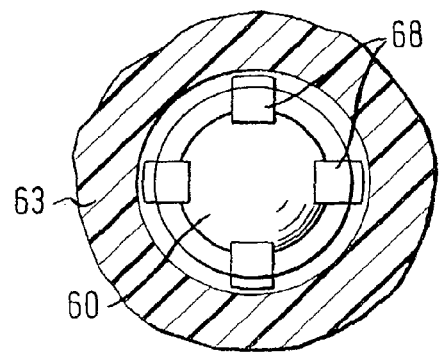

The third embodiment shown in FIGS. 3*a*-3*c* includes an X-ray contrast ball 60 which is inserted, together with a basket 62 formed as a plug, in a bore 66 of an element 63. The X-ray contrast ball 60 consists of metal, e.g. of titanium or tantalum, while at least the material of the element 63 is highly cross-linked ultra-high molecular weight polyethylene.

The basket 62 has a receiver 64 having four arms 68 arranged offset to one another by 90 degrees in a circle. The inner contour of the arms 68 is matched to the ball surface of the X-ray contrast ball. A respective projection 70 is provided at the outer side of the arms 68.

The bore 66 has recesses 72 arranged in a ring around its circular periphery for the receiving of the projections 70 in the pre-positioning location. The bore moreover has an inwardly arched, closed end 74.

In the pre-positioning location shown in FIG. 3*a*, the X-ray contrast ball 60 is loosely arranged between the basket 62 and the closed end 74 of the bore 66. In this connection, the basket 62 is held by means of a snap connection between the projections 70 and the recesses 72 with play on all sides of, for example, 0.2 mm. Only small-area contact points are present between the ball 60, the basket 62 and the bore 66.

The pre-positioning location is set at the manufacturer's. A gas sterilization with ethylene oxide then takes place. This covers the whole implant, since gas flows around all surfaces inside the bore through the open end of the bore and through the intermediate spaces between the arms 68. The basket 62 is installed in a force locked and shape matched manner so fixedly in the pre-positioning location that a release of the basket 62 and of the X-ray contrast ball 60 from the element 63 during transport is precluded.

The end positioning location shown in FIGS. 3*b* and 3*c* is achieved, starting from the pre-positioning location, by pushing the basket 62 towards the closed end 74 of the bore.

In this connection, the basket 62 is clamped in a tapering region of the bore 66 while the ball 60 is fixed in a force locked and shape matched manner between the arms 68 of the basket and the arched end 74 of the bore. The end of the basket 62 opposite the receiver 64 terminates in a flush manner with the open end of the bore 66 with a snap connection 61 in the end positioning location.

Fourth Embodiment

Figure 4A:
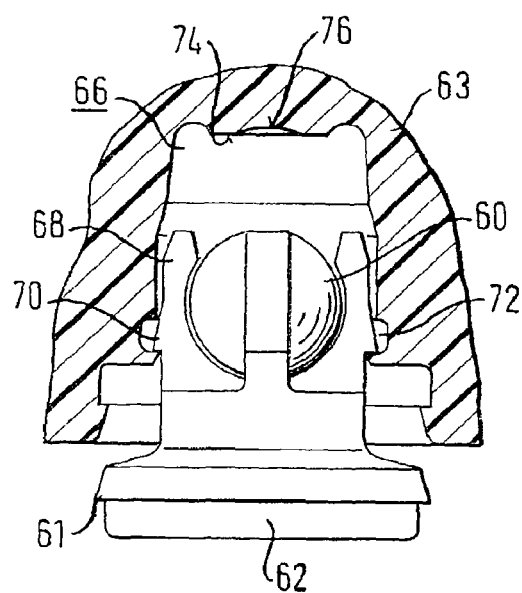
FIGS. 4a-4c are cross-sectional views of a fourth embodiment.
Figure 4B:
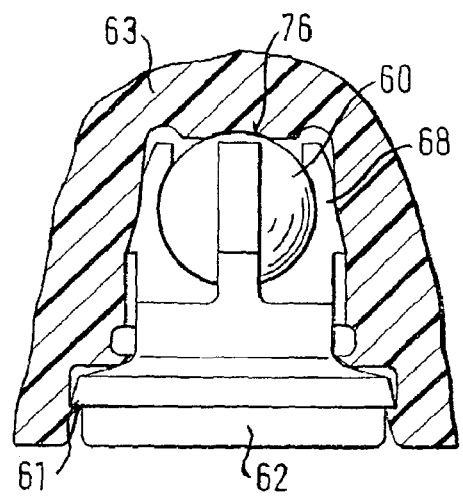
Figure 4C:
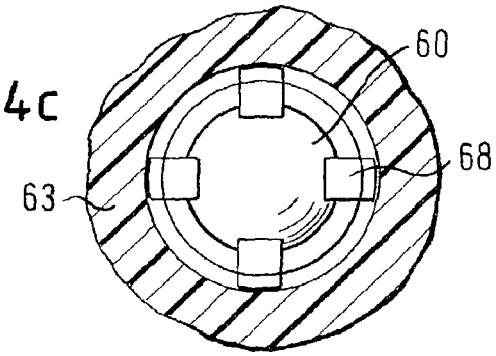

The fourth embodiment, which is shown in FIGS. 4*a* to 4*c*, corresponds to the third embodiment, with the X-ray contrast ball 60, however, as shown in FIG. 4*a*, already being held in the pre-positioning location in the receiver 64 of the basket. In this connection, a play at all sides of, for example 0.2 mm, is present between the ball 60 and the arms 68 due to the inner contour of the arms 68.

It is ensured in the pre-positioning location that sterilization gas can sufficiently flow around all surfaces inside the bore taking into account the relative movability. In this connection, the contact areas between the ball 60 and the arms 68 are of small area. The same applies to the contact points of the basket 62 with the implant 63 in the snap connection between the projections 70 and the recesses 72.

The end positioning location shown in FIG. 4*b* is set by a displacement of the basket in the direction of the closed end 74 of the bore starting from the pre-positioning position and is fastened by a snap connection 61. In the end positioning location, the ball 60 and the basket 62 are fixed in place in a force locked and shape matched manner at the end 74 of the bore.

Fifth Embodiment

Figure 5A:
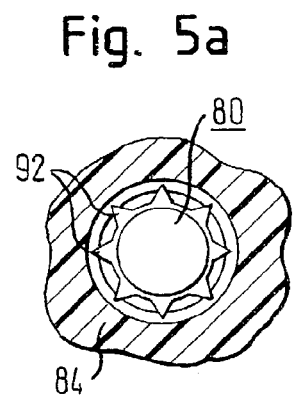
FIGS. 5a-5c are cross-sectional views of a fifth embodiment.
Figure 5B:
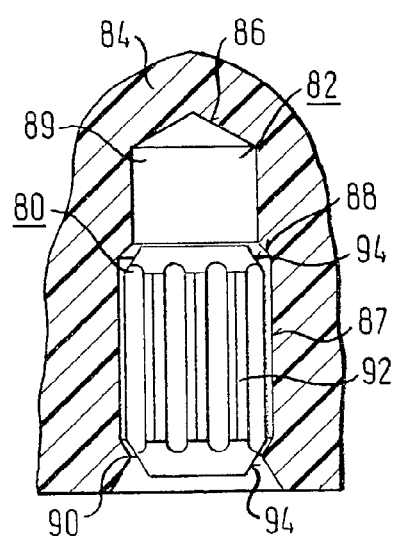
Figure 5C:
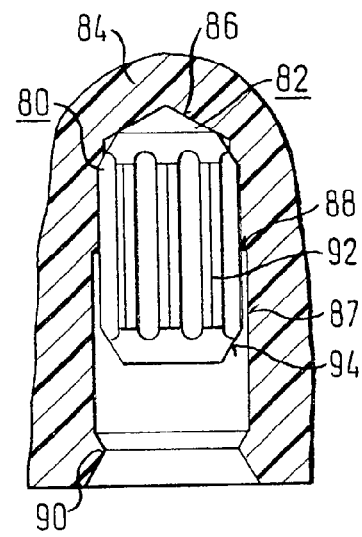

The fifth embodiment shown in FIGS. 5a to 5c includes an implant 84 of highly cross-linked UHMWPE having a bore 82 and an X-ray contrast pin 80 of metal.

The bore 82 has a region 87 with a large diameter at its open end. A region 89 with a smaller diameter is formed at the closed end of the bore 82. The bore 92 further has a tapering region 88 between the region 87 and the region 89 and an annular holding projection 90 in the region 89 arranged towards the open end of the bore.

The X-ray contrast pin 80 has teeth 92 distributed about the periphery and extending in the longitudinal direction.

The pre-positioning location is set at the manufacturer's by introducing the pin 80 between the tapering region 88 and the projection 90 of the bore. In this connection, the X-ray contrast pin 80 is held with a play of 0.2 mm axially. The teeth 92 hold the pin inside the region 87 with the large diameter in a radially centered manner with a play of 0.2 mm. The contact points of the tips of the teeth 92 with the inner wall of the bore 82 are linear. All surfaces at the interior of the bore 82 are thereby effectively sterilized with gas.

The end positioning location shown in FIG. 5c is set by pressing the pin 80 from the pre-positioning location in the direction of the closed end 86 of the bore. In this connection, the pin is clamped in a force locked and shape matched manner in the region 89 at the end 86 of the bore. The teeth 92 engage into the inner wall of the bore with a smaller diameter and in this manner fix the pin 80 in the bore 82.

Sixth Embodiment

Figure 6A:
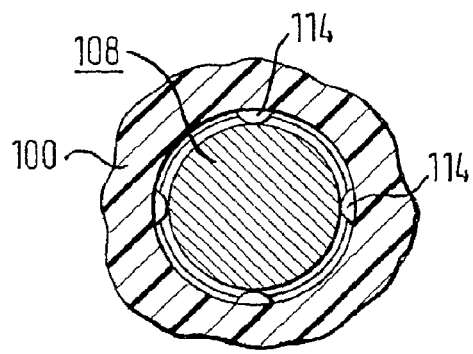
FIGS. 6a-6c are cross-sectional views of a sixth embodiment.
Figure 6B:
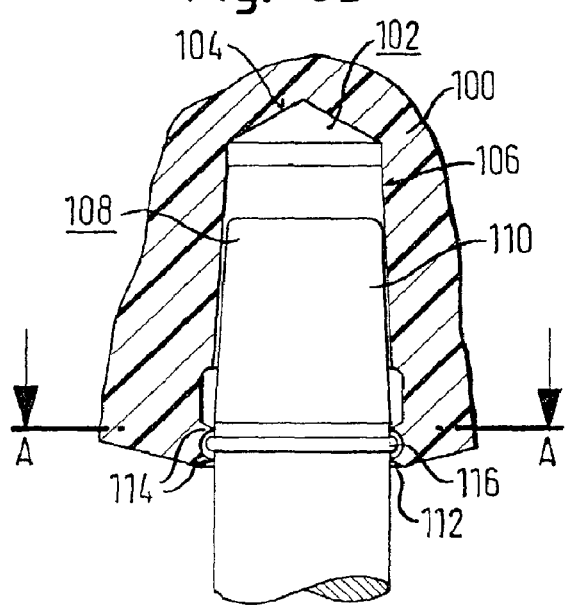
Figure 6C:
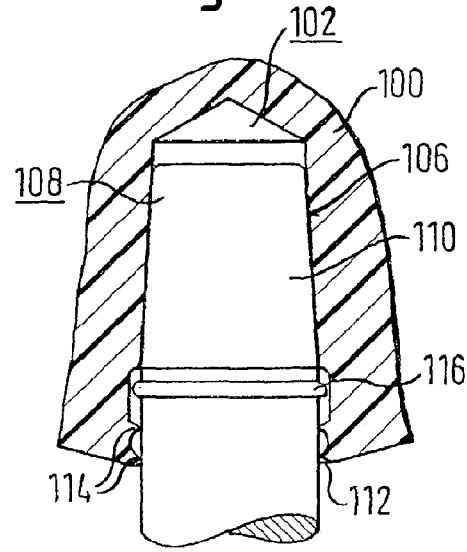

The sixth embodiment shown in FIGS. 6a to 6c includes a pin 108 of metal and an element 100 of UHMWPE. The pin 108 serves as a mechanical guide element to adjacent implant elements. The pin 108 is, for example, anchored as a bolt in a movable tibia insert (gliding meniscus) of highly cross-linked UHMWPE for guiding with respect to a tibia metal reinforcement.

The pin 108 has a conical end 110 and an annular projection 116 which is arranged adjacent to the conical end 110.

The element 100 contains a bore 102 having a region 106 complementary to the conical end 110 of the pin. The bore 102 furthermore has projections 114 at its open end 112 which are provided in the form of two rings arranged parallel to one another about the periphery of the bore.

The projection 116 is held in the pre-positioning location between the two rings of the projections 114 with play axially and radially. In this connection, the conical end 110 of the pin is likewise mounted with play in the region 106 of the bore. The contact points between the projections 114 and the pin 108 are spot shaped, as can be recognized from FIG. 6a.

The radial and axial play and the punctiform contact points ensure that sterilization gas flows around practically all surfaces within the bore 102 in the sterilization.

An end positioning location of the pin 108 shown in FIG. 6c is set, starting from the pre-positioning location, by pressing the pin 108 in the direction of the closed end 104 of the bore. In this connection, the conical end 110 of the pin is clamped in the region 106 of the bore complementary thereto. The projection 106 of the pin 108 is now located in a cross-sectional region of the bore 102 which is provided between the projections 114 and the conically tapering region 106. The free path of the projection 116 in the longitudinal direction of the bore ensures that the conical anchoring is not impaired on the setting of the end positioning location.

Seventh Embodiment

The seventh embodiment shown in FIGS. 7a to 7c includes a pin 128 of metal and an element 120 of UHMWPE.

The pin 128 has a conical end 130. The pin 128 further has two recesses 138 and 140 which are arranged behind one another adjacent to the conical end 130 and are each introduced in an annular manner into the pin 128. The annular recess 138 arranged directly behind the conical end 130 of the pin has a contour matched to projections 134 at the element 120, while the recess 140 is made larger in the longitudinal direction of the pin 128 in comparison with the recess 138.

A bore 122 is provided in the element 120 which has a region 126 complementary to the conical end 130 of the pin. The bore 122 has the projections 134 at the open end 132 which are distributed in a ring about the periphery of the bore. A region 136 of the bore, whose cross-section is larger than that of the region 126, lies between the projection 134 and the conically tapering region 126.

The pre-positioning location is set at the manufacturer's before the gas sterilization by inserting the pin 128 into the bore 122.

FIGS. 7a and 7b show the pin 128 in the pre-positioning location in which the pin 128 is loosely held with a radial and axial play of, for example, 0.2 mm by bringing into engagement of the projections 134 with the recesses 138. In this connection, the conical end 130 of the pin is likewise loosely received within the conically tapering region 126 of the bore. It can be seen from FIG. 7a that exclusively punctiform contact points having play exist between the projections 134 and the pin 128.

The play between the surfaces of the pin 128 and the inner walls of the bore 122 ensures that sterilization gas flows sufficiently around practically all surfaces within the bore 122. The sterile transport of the implant also takes place in the pre-positioning location.

After the opening of the packaging and shortly before the insertion of the implant 120, the pin 128 is fixed in place, starting from the pre-positioning position, by pressing the pin into the bore in the end positioning location shown in FIG. 7c. In this connection, the conical end 130 of the pin sits fixedly in a force locked and shape matched manner in a clamping location in the region 126 of the bore.

Eighth Embodiment

Figure 8C:
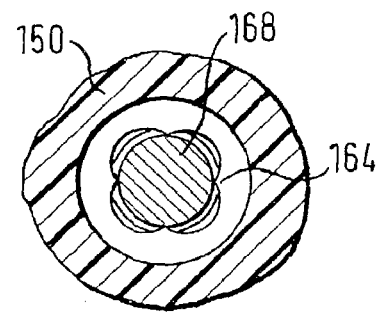
FIGS. 8a-8c are cross-sectional views of an eighth embodiment.
Figure 8A:
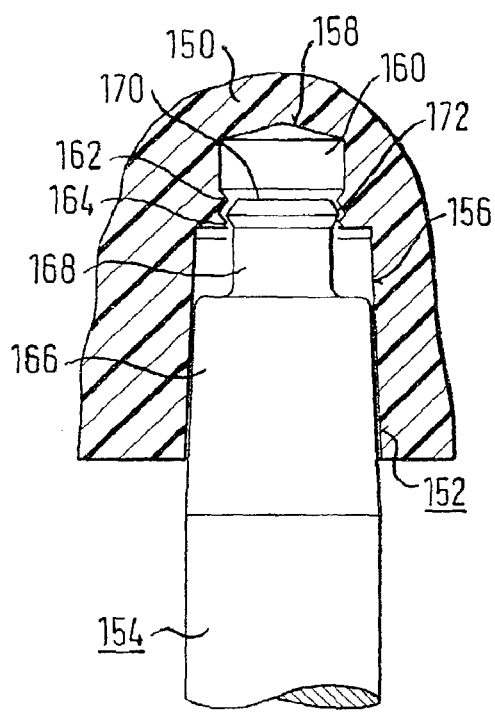
Figure 8B:
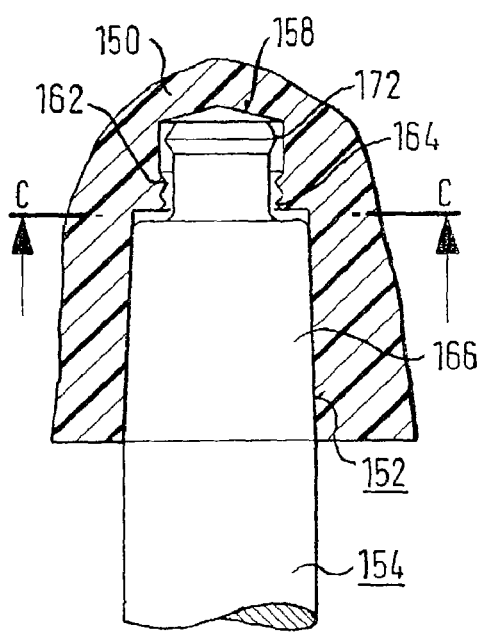

FIGS. 8a to 8c show the implant in accordance with the invention designed as a conical connection between an implant 150 with a bore 152 and pin 154. The implant 150 consists of highly cross-linked ultra-high molecular weight polyethylene, whereas the pin 154 is a metal pin.

The pin 154 has a conical region 166 which is adjoined by a spigot 168. The diameter of the spigot is smaller than the diameter of the conical region 166. A annular projection 172 is formed at the flat front end 170 of the spigot 168 around the periphery.

The bore 152 has a conical region 156 complementary to the conical region 166 of the pin 154. A region 160 having a smaller diameter in comparison with the conical region 156 is provided between this and the closed end 158 of the bore 152. The region 160 has projections 162, 164 running toward a tip into the interior of the bore at is entrance, said projections 162, 164 forming ring parts following one another axially.

The pre-positioning location shown in FIG. 8a is set by introducing the pin 154 into the bore 152 and latching the projection 172 in the intermediate space between the projections 162 and 164. In this connection, the projection 172 of the pin 154 is held between the projections 162 and 164 with a radial and axial play. The conical region 166 of the pin is loosely held with play in the conical region 156 of the bore. The contact points having play between the pin 154 and the projections 162, 164 are punctiform due to the shape of the projections.

It is thus ensured that the sterilization gas can act on practically all surfaces within the bore 152.

The end positioning location shown in FIGS. 8b and 8c is set shortly before implanting, starting from the pre-positioning location, by pressing the pin 154 in the direction of the closed end of the bore 152. In this connection, the pin 154 sits in a force locked and shape matched manner with its conical region 166 in the bore.

Ninth Embodiment

Figure 9C:
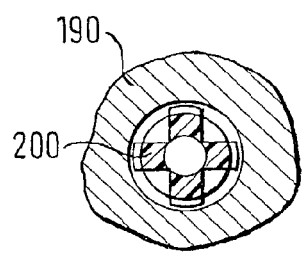
FIGS. 9a-9c are cross-sectional views of a ninth embodiment.
Figure 9A:
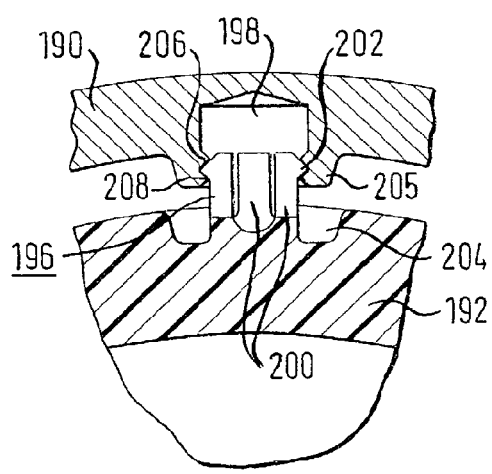
Figure 9B:
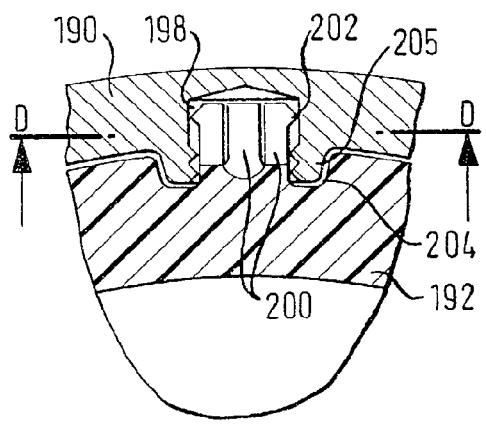

The ninth embodiment shown in FIGS. 9a to 9c relates to an implant consisting of an outer shell 190 and an inner shell 192, for example for a hip joint prosthesis. The outer shell 190 consists of a metal, for example of a titanium alloy, and the inner shell is formed of highly cross-linked ultra-high molecular weight polyethylene. This is held in a centered manner in a pre-positioning location in the outer shell 190 by means of a snap spring 196 of the inner shell and by means of a recess 198 in the outer shell 190.

The snap spring 196 of the inner shell consists of four resilient webs 200 arranged offset by 90 degrees in a circle. A respective projection 202 is provided at the outer side of the webs 200 at the free end of the webs.

The recess 198 has, at its open end, two annular projections 206 and 208 arranged parallel to one another about the periphery of the recess 198.

The pre-positioning position shown in FIG. 9a is set before the gas sterilization of the implant. In this connection, the webs 200 are held in a snap connection with their projections 202 between the projections 206 and 208 of the recess. The contact points are small in area and have radial and axial play. An intermediate space which is large in comparison with this play of, for example, 0.2 mm is present between the other surfaces of the outer shell 190 and of the inner shell 192. This intermediate space and the play of the snap connection between the projections 202, 206 and 208, as well as the intermediate spaces between the webs 200, ensure that practically all surfaces within the recess 198 can be reached by the sterilization gas during sterilization.

The end positioning is realized by displacement of the inner shell 192 from the pre-positioning location in the direction of the outer shell 190, wherein the projection 202 of the snap spring is pressed over the projection 206. As shown in FIGS. 9b and 9c, the snap spring 196 is here inserted almost completely into the recess 198 and centers the inner shell 192 in the outer shell 190, with the projection 206 of the outer shell engaging in a shape matching manner into a corresponding recess 204 of the inner shell 192. The actual anchoring between the outer and the inner shell takes place by a snap connection at the equator.

Tenth Embodiment

The tenth embodiment of the implant in accordance with the invention shown in FIGS. 10a to 10d relates to a spigot anchoring. It includes a pin 210 of metal which has an anchoring part 212 and a flange 213 as well as an implant 214 with a bore 216.

The bore has a region 217 with a small diameter in front of the closed end 218 and a region 219 with a larger diameter between this and the open end. A region 220 tapering towards the closed end 218 of the bore is provided between the regions 217 and 219. A projection 222 around the periphery of the bore is provided with a spacing from the tapering region 220 in the entrance region 219 of the bore.

The pin 210 has two sections 224 and 226 which are provided with teeth 228 extending in the longitudinal direction of the pin. In the sections 224 and 226, the pin thus has a star-like cross-section shown in FIG. 10b. The sections 224 and 226 are separated by a section 230 which is not provided with teeth and which has a smaller cross-section than the sections 224 and 226.

The pre-positioning location shown in FIGS. 10a and 10b is set before the carrying out of a gas sterilization, in particular of a sterilization with ethylene oxide. In this connection, the section 224 of the pin is arranged between the tapering region 220 and the projection 222 of the recess. In this position, radial play exists between the pin and the inner wall of the recess due to the teeth 228 which hold the pin centered inside the recess. Axial play is also present. The contact points are punctiform and have play in the pre-positioning location between the teeth 228 and the implant 214. Practically all surfaces within the bore 216 can thus be reached by the gas in the gas sterilization.

The end positioning location shown in FIGS. 10c and 10d is reached, starting from the pre-positioning location, shortly before the insertion of the implant by pressing the pin 210 into the bore 216 and digging in of the teeth 228 into the inner wall of the bore 216. The pin 210 is in this manner anchored rotationally fixedly in the bore 216. The flange 213 of the anchoring part 212 here terminates in a flush manner, arranged in a recess, with the open end of the bore 216 so that only the anchoring part 212 projects out of the implant 214.

The anchoring part 212 can be used as a rotationally fixed base for other elements of the implant. The anchoring part 212 can here be made rotationally symmetrically with respect to the pin 210, as an eccentric spigot or as a forked receiver. The bifurcation of the receiver is aligned interoperatively as necessary on setting the end positioning.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of sterilizing an implant, the implant comprising at least a first element and a second element, the method comprising the steps of:

positioning the first element in a pre-positioning location with respect to the second element, the first element capable of moving relative to the second element but constrained from separation from the second element in the pre-positioning location; and sterilizing the implant while the first element is in the pre-positioning location with respect to the second element;

wherein the implant is configured to allow the first element to move to an end positioning location with respect to the second element, and wherein the first element engages the second element such that relative movement between the first element and the second element is prevented in the end positioning location.

2. The method of claim 1, further comprising the steps of:
providing the first element constructed of one of a metal and a plastic; and
providing the second element constructed of one of a metal and a plastic, the second element being constructed of a material different than the first element.

3. The method of claim 1, wherein the positioning step comprises providing the first element with at least one of radial and axial play relative to the second element in the pre-positioning location.

4. The method of claim 1, wherein the positioning step comprises positioning the first element at least partially within a recess of the second element.

5. The method of claim 4, wherein moving the first element within the recess of the second element moves the first element from the pre-positioning location to the end positioning location.

6. The method of claim 1, wherein moving the first element to the end positioning location increases contact between the first element and the second element compared to the pre-positioning location.

7. The method of claim 1, further comprising the step of packaging the implant while the first element is in the pre-positioning location with respect to the second element prior to the sterilizing step.

8. The method of claim 1, wherein the sterilizing step comprises subjecting the implant to a gas.

9. The method of claim 1, further comprising the step of transporting the implant with the first element in the pre-positioning location with respect to the second element after the sterilizing step.

10. The method of claim 1, wherein moving the first element from the pre-positioning location to the end positioning location includes at least one of rotating and translating the first element relative to the second element.

11. The method of claim 1, wherein the implant is configured to allow the first element to frictionally engage the second element in the end positioning location.

12. A method of sterilizing an implant comprising the steps of:
providing an implant comprising a first element and a second element, the second element having a recess;
positioning the first element in a pre-positioning location with respect to the second element, the first element at least partially located in the recess of the second element and constrained from separation from the second element in the pre-positioning location; and
subjecting the implant to a sterilization gas while the first element is in the pre-positioning location with respect to the second element, the sterilization gas capable of traveling between the first element and the second element when the first element is in the pre-positioning location;
wherein the implant is configured to allow the first element to move to an end positioning location with respect to the second element, and wherein the first element is prevented from moving relative to the second element in the end positioning location.

13. The method of claim 12, wherein the recess includes a closed end and wherein the implant is configured to prevent a gas from traveling between the first element and the second element to the closed end of the recess when the first element is in the end positioning location.

14. The method of claim 12, wherein the recess includes a closed end and the sterilization gas is capable of traveling to the closed end of the recess when the first element is in the pre-positioning location.

15. The method of claim 12, wherein the positioning step comprises providing the first element with at least one of radial and axial play relative to the second element in the pre-positioning location.

16. The method of claim 12, wherein the recess includes a closed end and the implant is configured to allow movement of the first element toward the closed end of the recess of the second element when the first element is moved from the pre-positioning location to the end positioning location.

17. The method of claim 12, wherein moving the first element from the pre-positioning location to the end positioning location includes at least one of rotating and translating the first element in the recess relative to the second element.

18. The method of claim 12, wherein moving the first element to the end positioning location includes increasing contact between the first element and the second element compared to the pre-positioning location.

19. The method of claim 12, wherein the implant is configured to allow the first element to frictionally engage the second element in the end positioning location.

20. A method of sterilizing an implant, the implant comprising at least a first element and a second element, the method comprising the steps of:
positioning the first element in a pre-positioning location with respect to the second element, the first element capable of moving relative to the second element but constrained from separation from the second element in the pre-positioning location; sterilizing the implant while the first element is in the pre-positioning location with respect to the second element; and
wherein the implant is configured to allow the first element to move to an end positioning location with respect to the second element, and wherein contact is increased between the first element and the second element when the first element is in the end position location compared to the pre-positioning location.

21. The method of claim 20, wherein the positioning step comprises providing the first element with at least one of radial and axial play relative to the second element in the pre-positioning location.

22. The method of claim 20, wherein the positioning step comprises positioning the first element at least partially within a recess of the second element.

23. The method of claim 20, wherein moving the first element from the pre-positioning location to the end positioning location includes at least one of rotating and translating the first element relative to the second element.

24. The method of claim 20, wherein the implant is configured to allow the first element to frictionally engage the second element in the end positioning location.

* * * * *